United States Patent [19]

Manning

[11] 4,056,490

[45] Nov. 1, 1977

[54] DEHYDROGENATION PROCESS AND CATALYST

[75] Inventor: Harold E. Manning, Houston, Tex.

[73] Assignee: Petro-Tex Chemical Corporation, Houston, Tex.

[21] Appl. No.: 634,207

[22] Filed: Nov. 21, 1975

Related U.S. Application Data

[63] Continuation of Ser. No. 477,401, June 7, 1974, abandoned.

[51] Int. Cl.$^2$ .................. B01J 23/00; B01J 27/06; C01G 37/14
[52] U.S. Cl. .................. 252/468; 252/441; 423/596
[58] Field of Search ............. 252/441, 468; 423/596

[56] References Cited

U.S. PATENT DOCUMENTS

| | | | |
|---|---|---|---|
| 1,632,299 | 6/1927 | Kränzlein et al. | 423/596 |
| 2,161,984 | 6/1939 | Sweeney et al. | 252/435 X |
| 2,205,141 | 6/1940 | Heard | 423/596 X |
| 2,209,458 | 7/1940 | Heard et al. | 252/468 X |
| 2,638,455 | 5/1953 | Pitzer | 252/465 |
| 3,781,376 | 12/1973 | Manning | 260/683.3 |
| 3,801,672 | 4/1974 | Bajars | 252/468 X |

OTHER PUBLICATIONS

Mellor Comprehensive Treatise on Inorganic and Theoretical Chemistry, vol. XI, p. 199, (1931).

Primary Examiner—Patrick P. Garvin
Assistant Examiner—William G. Wright
Attorney, Agent, or Firm—Kenneth H. Johnson

[57] ABSTRACT

Magnesium chromite dehydrogenation catalyst are improved by preparation in oxygen deficient or essentially inert calcination atmospheres and in the presense of halogen, either singularly or in combination.

17 Claims, No Drawings

DEHYDROGENATION PROCESS AND CATALYST

This is a continuation of application Ser. No. 477,401 filed June 7, 1974, now abandoned.

BACKGROUND OF THE INVENTION

This invention relates to a process for the dehydrogenation of gaseous hydrocarbons and the catalyst employed. More specifically the process is a cyclic process wherein there are alternating cycles of dehydrogenation and catalyst regeneration.

The process is a cyclic process in which gaseous hydrocarbons such as butane, isopentane or ethylbenzene are dehydrogenated over a suitable catalyst to produce butenes and butadiene, isopentene and isoprene and styrene, respectively. After each dehydrogenation cycle there is a catalyst regeneration cycle in which the accumulated coke is burned off by passing molecular oxygen through the catalyst followed by another dehydrogenation cycle and so on.

The chromia-alumina catalysts have been recognized for a number of years as the most preferred catalysts for this type of process. The chromia-alumina catalysts are prepared by treating activated alumina with a solution of chromic acid, draining off the excess acid from the alumina, drying and heat treating at about 400° F. Commercial chromia-alumina dehydrogenation catalysts normally contain about 20% chromium oxide. preparative methods are shown, for example, in U.S. Pat. Nos. 2,399,678 and 2,419,997.

Other chromia-metal oxide materials have been investigated for their dehydrogenation capabilities. One of the more prominent among these has been chromia-magnesia which has been found to be a poor second to chromia-alumina. Several patents were issued to Tropsch in the late 1930's relating to magnesia based chromia dehydrogenation catalysts, e.g., U.S. Pat. Nos. 2,122,786; 2,122,787; 2,122,790; and 2,148,140. Pitzer disclosed chromia-magnesia-alumina dehydrogenation catalyst in U.S. Pat. No. 2,638,455. U.S. Pat. No. 3,781,376, discloses magnesium chromites promoted with aluminum.

It is a principal feature of the present invention that improved magnesium chromite catalysts have been developed. It is another feature of the present invention to find a catalyst superior to the chromia-alumina catalysts for use in dehydrogenation. it is still an advantage that a process which will give better results than presently achieved with chromia-alumina catalysts has been provided. Other features and advantages of the present invention will be apparent from the following description.

SUMMARY OF THE INVENTION

The present invention relates to two variables which have been found to effectively interrelate to provide superior magnesium chromite catalyst for use in dehydrogenations. In one aspect of the invention, magnesium chromites are prepared by reacting the chromite precursors in a relatively oxygen deficient atmosphere, that is, an atmosphere containing less oxygen than air, less than 20 mol percent oxygen, or more preferably less than 15 mol percent. In another aspect of the invention the magnesium chromite is prepared by reacting the precursors thereof in the presence of halogen. A particularly superior magnesium chromite for use in dehydrogenation is prepared by the reaction of the precursors of magnesium chromite in the presence of halogen in an atmosphere containing less than 20 mol percent oxygen. The present invention also relates to the processes of de-hydrogenation employing the improved catalysts.

DETAILED DESCRIPTION OF THE INVENTION

The catalysts of this invention contain magnesium, chromium and oxygen which are chemically combined in such a manner as to form a definite and discrete inorganic chemical compound generally referred to in the literature as magnesium chromite. This chromite, like many other chromites, is isostructural to the mineral spinel (magnesium aluminate) and consequently can be said to have the spinel structure which is of a face-centered cubic form.

The catalysts of the present invention are predominately chromites, that is, they contain more than 50% by weight of the chromite. Preferably the catalysts contain 75% or more chromites, i.e., 90% chromites. The chromites generally may be represented by the formula $MeCr_2O_4$ where Me as stated above is Mg, however, a portion of the magnesium an be replaced with other metals having an ionic radius approximately between about 0.5 and 1.1A, preferably between about 0.6 and 1.0A. In the case of such mixed chromites, Mg will be the predominant Me ion, comprising at least 50 atomic % of the Me ions present. In addition to Mg the Me may be one or more of the divalent ions of Ca, Sr, Ba, Fe, Mn, Co, Ni, Cu, Zn, or Cd.

The magnesium chromites of the present invention exhibit a certain type of X-ray diffraction pattern. The peaks observed in the X-ray diffraction pattern may not have sharp peaks such as those found, e.g., in highly crystalline material of the same chemical composition, but can and do frequently exhibit relatively broad reflection peaks. The degree of sharpness of the reflection peak may be measured by the reflection peak band width at half height ($W/h/2$). In other words, the width of the reflection peak as measured at one-half of the distance to the top of the peak is the "band width at half height." The band width at half height is measured in units of °2theta. Techniques for measuring the band widths are discussed, e.g., in Chapter 9 of Klug and Alexander, X-ray Diffraction Procedures, John Wiley and Son, N.Y., 1954. The observed band widths at half height of the preferred compositions of this invention are at least 0.12°2 theta and normally will be at least 0.16°2 theta.* The particular reflection peak used to measure the band width at one-half height is the reflection peak having Miller (hkl) indices of 111. (See, e.g., Chapter of Klug and Alexander, ibid). This description is not to be taken as a limitation of the invention in regard to the relationship between composition activity and band width.

*The powder diffraction patterns may be made, e.g., with a Norleco constant potential diffraction unit type No. 12215/0, equipped with a wide range goniometer type No. 42273/0, copper tube type No. 32147, proportional counter type No. 57250/1; all coupled to the Norelco circuit panel type No. 12206/53. The copper K alpha radiation is supplied by operating the tube at a constant potential of 40 kilovolts and a current of 35 milliamperes. A nickel filter is used to remove K beta radiation. The detector voltage is 1600 volts and the pulse height analyzer is set to accept pulses with amplitudes between 10 and 30 volts only. Slits used are divergence 1°, receiving 0.006 inches and scatter 1°. Strip chart recordings for identification are made with a scanning speed of 1° per minute, time constant of 1 second and a full scale at 10³ counts per second. No correction is made for $K_a$ doublet or instrumental broadening of the band widths.

Suitable catalyst according to this invention is magnesium chromite having X-ray diffraction peaks with the d-spacings 4.80–4.82, 2.94–2.96, 2.50–2.52, 2.40–2.42, 2.07–2.09, 1.90–1.92, 1.69–1.71, 1.59–1.61, 1.46–1.48, 1.40–1.42, and the most intense peaks being between 2.50–2.52.

Chromite formation can be accomplished by reacting an active compound of chromium with an active compound of magnesium and the other designated metals. By active compound is meant a compound which is reactive under the conditions to form the chromite. Starting compounds of chromium, magnesium or the other metals may be such as the nitrates, hydroxides, hydrates, oxalates, carbonates, acetates, formates, halides, oxides, etc.

The catalyst may contain an excess of chromium over the stoichiometric amount, which is 2 atoms of chromium per atom of Me (MeCr$_2$O$_4$). There may be from 10 to 200 percent excess of the chromium. Similarly the Me portion of the chromite may be present in more than a stoichiometric amount.

The magnesium chromite can be prepared by precipitation, dry or wet milling or mixing, by precipitation of one of the ingredients in the presence of the other, coprecipitation and impregnation of one or more of the solid ingredients with aqueous or non-aqueous solutions of salts of the ingredients.

The present invention has been found to be particularly beneficial when the magnesium chromite has been prepared by intimate mixing of the solid components, such as by a slurrying procedure.

A particularly preferred magnesium chromite is one such as described and claimed by the present inventor in U.S. Pat. No. 3,781,376 wherein the magnesium chromite contains aluminum therein; and the disclosure of that patent in regard thereto is incorporated herein. The preferred catalyst contains chromium, magnesium, aluminum and oxygen. The catalyst are characterized as magensium chromites either in admixture with aluminum oxide or containing aluminum therein and can be considered as aluminum promoted magnesium chromites.

The aluminum component of the catalyst may also be present as a constituent of the chromite, however, it is not necessary that the aluminum be a portion of the chromite and may be present in addition to the metal chromite in the form of aluminum oxide. The aluminum can be incorporated into the chromite by backing out a portion of the chromium. Aluminum can be substituted for up to less than 50% of the chromium atoms of the chromite. Such chromites have the formula MeAl$_x$Cr$_{2-x}$O$_4$ where Me has the designation previously given and $x$ is a number of from more than 0 up to less than 1.

The aluminum component of the catalyst can be added prior to and/or after the calcination and formation of the chromite. The aluminum component is conveniently added to the chromite as a soluble salt in a slurry with the chromite after which it is dried; then decomposed by heating to aluminum oxide. Alternatively insoluble aluminum oxide can be added to the magnesium chromite, preferably in a highly divided state. Yet another desirable way to place the aluminum in the catalyst is by coprecipitation of aluminum hydroxide with the Me hydroxide and chromium hydroxide.

The aluminum will be present in the catalyst in all forms in an atomic ratio of Al:Cr of 0.0004 to 1.2.:1. For example, in terms of a soluble aluminum compound such as aluminum sulfate, added to the magnesium chromite this would represent from about 0.1 to 75 weight percent Al$_2$(SO$_4$)$_3$.16H$_2$O based on the total weight of the catalyst. A preferred range of Al:Cr atom ratio is 0.04 to 0.8:1. Generally the higher weight percentages of aluminum compound, i.e., 50 weight percent or more, are applied to the magnesium chromites having high surface areas, e.g., 50m$^2$ per gram or more.

The active catalysts can be pelleted or applied to a suitable support, such as alumina, silica gel, slicaalumina, firebrick, kieselguhr, quartz and the like. The catalyst is the active surface available for contact with the gaseous reactants.

The formation of the chromite is obtaind by heating the slurry or other intimate mixture of chromite precursors at an elevated temperature, e.g., 400°–1100° C (generally no greater than 1300° C), in a controlled atmosphere, as described below, i.e., usually 5 minutes to 4 hours. A calcination temperature of 550°–900° C has been found particularly useful and temperature in the range of 600°–800° C have been found to produce excellent catalysts.

It has now been discovered that improved magnesium chromites may be formed by preparing the magnesium chromite in a particular manner. It has also been discovered that these compositions of matter exhibit superior catalytic qualities such as for the dehydrogenation of organic compounds and for other uses. According to this invention the magnesiun chromite is formed in an atmosphere containing less oxygen than normally contained in air, such as less than 15 or 20 mol percent oxygen. By thus causing the reaction to take place in an atmosphere deficient in oxygen, the metal portion of the chromite is less prone to be oxidized to a higher valence. The reaction to form the chromite is preferably essential in the absence of oxygen, preferably a non oxidizing atmosphere, such as in an atmosphere of nitrogen or helium. The nature of a preferred atmosphere used to calcine or sinter the metal chromite precursors is one in which the reactants and the metal chromites produced are essentially inert. Thus the atmosphere would be an essentially inert atmosphere rather than either an essentially oxidizing atmosphere or an essentially reducing atmosphere, although small quantities of non-inert gases, e.g., either or both of oxidizing or reducing gases, or other reactive gases, i.e., about up to 3 mol percent would be acceptable in the preferred embodiment. As defined herein an inert atmosphere comprises essentially nitrogen, helium, neon, argon, krypton, xenon, radon, and mixtures thereof.

The appearance of reactive gases in the calcining atmosphere often occurs in large scale preparation when the exclusion of the atmospheric gases from conventional and available equipment is a practical impossibility. There is also the possibility of the buildup of reactive gases from the by-products of the calcination step, e.g., carbon dioxide and steam. The presence of such reactive gases in the calcining atmosphere raises an important consideration to be observed in the operation of the process. If the atmosphere in the calciner were to remain stationary, that is, not removed or replenished during the calcining even for a considerable duration then 3 mol percent of the reactive gas in the atmosphere is acceptable. However, in practice it is more likely that the atmospher will be renewed, that is, a moving atmosphere passing in and around or over the catalyst.

In a moving or renewed atmosphere even low concentrations of reactive gases can have a cumulative effect so that, for example, a nitrogen atmosphere containing only 3 mol percent of oxygen which is passed through a reactor for 70 hours at 800° C over a catalyst will produce a chromite essentially the same as if the calcining had been carried out in air. Thus, the permissible concentration of reactive gases in a moving atmosphere will be determined in part by the duration of the calcining. Calcining as described elsewhere herein carried on for up to about 5 hours, generally will show little or no cumulative effect of the reactive gases present.

It is a further aspect of the present invention that a halogen be present during the magnesium chromite formation. The exact function of the halogen is not fully understood. Apparently, the halogen catalyzes the solid state reaction of the precursor ingredients to form the magnesium chromite product.

The halogen may be present in any suitable form wherein the halogen can be in intimate contact with the reactants during chromite formation. The halogen may be present in the reaction atmosphere as molecular halogen or as volatile halogen compounds such as HX or $NH_4X$. However, a preferred method is to introduce the halogen by way of a solid inorganic compound which at least partially decomposes during chromite formation. Chromium or magnesium halides (or hydrates thereof) are entirely satisfactory and desirable. Generally the halogen will be chlorine, bromine or iodine with chlorine being the preferred halogen. Suitable sources of halogen are such as $Cl_2$, $Br_2$, $I_2$, HCl, HBr, HI, $NH_4Cl$, alkyls halides containing 1 to 6 carbon atoms such as methyl chloride, halohydrins such as ethylene chlorhydrin, halosubstituted aliphatic acids such as chloroacetic acid, organic amine halide salts of the general formula $R_3N.HX$ wherein R is a hydrocarbon radical containing from 1 to 8 carbon atoms such as methyl amine hydrochloride or hydrobromide and other halogen compounds such as $CrBr_3$, $CrCl_3$, $CrF_3$, $MgCl_2$, $MgBr_2$, $CCl_4$ and the like; or $MnCl_2.4H_2O$, $MnI_2$, $FeCl_3.6H_2O$, $FeF_2$ or the like where a portion of the Mg is to be replaced in the chromite.

Generally, halide compounds will be used which require a temperature of no greater than 450° C to exert a vapor pressure of at least 1 mm of Hg at atmospheric pressure. Data showing the temperature necessary to achieve 1 mm of Hg vapor pressure of various metal halides may be found on page 650 of Industrial and Engineering Chemistry, Vol. 39, No. 4, April 1947, which article is incorporated herein by reference. However, halogen compounds other than those listed in that reference are useful according to this invention. Ordinarily, the halogen compound will have from 0 to 8 carbon atoms and will have a molecular weight of less than 750. As mentioned, the function of the halogen is not fully understood. Furthermore, the actual mechanism during the reaction is also not fully understood. However, it is generally thought to be desirable to have the halogen present in an amount of from 0.0001 to 1.0 mols of halogen (calculated as mols of halogen, $X_2$) per atom of chromium present in the chromite reactants. This halogen may be present either in the solid phase, volatile phase or combinations thereof. Generally speaking, the vapor atmosphere present during chromite formation (which is considered at the temperature at which chromite can first be detected and usually will be at a temperature of at least 250° to 350° C) will contain from 0.0001 to 3 mol percent of halogen (calculated as mols percent of $X_2$), and preferably from 0.01 to 1 mol percent of the atmosphere. These ratios may be varied somewhat depending upon reaction conditions, and other considerations as stated herein.

In a particular embodiment of the present invention water insoluble or essentially insoluble precursors of magnesium chromite such as, for example, fine powders of $MgCO_3$, $MgCO_3.Mg(OH)_2.3H_2O$, $MgF_2$, MgO, $MgSiO_3$, CrO, CrB, $Cr_3C_2$, CrN, $CrO_2$, $Cr_2O_3$, $Cr_2O_3.XH_2O$, $2Cr_2O_3.CrO_3.XH_2O$ and the like are slurried to form an intimate mixture of the components (including halogen components if any). This mixture is then dried, preferably at temperatures below about 150° C or at about 100°–135° C. The dried material is then calcined as indicated above. The calcined material will contain magnesium chromite, as has been established by X-ray diffraction analysis. This material in this embodiment is then mixed in a slurry with an aluminum component, deposited on a support and dried.

The catalysts of this invention can be applied to the dehydrogenation of a wide variety of organic compounds, particularly parafin and olefin hydrocarbon compounds. Such compounds normally will contain from 2 to 20 carbon atoms, at least one

grouping, having a boiling point below about 350° C, and may contain other elements, in addition to carbon and hydrogen such as oxygen, halogens, nitrogen and sulfur. Preferred are compounds having 2 to 12 carbon atoms, and especially preferred are compounds of 3 to 8 carbon atoms.

Representative materials which are dehydrogenated by the novel process of this invention include n-butane, ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 1,3-dichlorobutane, 1,4-dichlorobutane, the chlorofluoroethanes, methyl pentane, methylethyl ketone, diethyl ketone, n-butyl alcohol, methyl propionate, isobutane, ethylbenzene and the like.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes and the like.

Suitable dehydrogenation reactions are the following: acyclic compounds having 4 to 5 non-quaternary contiguous carbon atoms to the corresponding olefins, diolefins or acetylenes having the same number of carbon atoms; aliphatic hydrocarbons having 6 to 16 carbon atoms and at least one quaternary carbon atom to aromatic compounds, such as 2,4,4-trimethylpentene-1 to a mixture of xylenes; acyclic compounds having 6 to 16 carbon atoms and no quaternary carbon atoms to aromatic compounds such as n-hexenes to benzene; cycloparaffins and cycloolefins having 5 to 8 carbon atoms to the corresponding olefin, diolefin or aromatic compound, e.g., cyclohexane to cyclohexene or cyclohexadiene or benzene; aromatic compounds having 8 to 12 carbon atoms including one or two alkyl side chains of 2 to 3 carbon atoms to the corresponding aromatic with unsaturated side chain such as ethyl benzene to styrene.

Illustration of dehydrogenations include butane to butenes and butadiene propionitrile to acrylonitrile;

propionaldehyde to acrolein; ethyl chloride to vinyl chloride; methyl isobutyrate to methyl methacylate; 2 to 3-chlorobutene-1 or 2,3-dichlorobutane to chloroprene; ethyl pyridine to vinyl pyridine; ethylbenzene to styrene; isopropylbenzene to $\alpha$-methyl styrene; ethylchlorohexane to styrene; cyclohexane to benzene; ethane to ethylene to acetylene; propane to propylene or methyl acetylene or allene; isobutane to isobutylene; n-butane to butene and butadiene-1,3; n-butene to butadiene-1,3 and vinyl acetylene; methyl butene to isoprene; cyclopentane to cyclopentene and cyclopentadiene; n-octane to ethyl benzene and orthoxylene; monomethylheptanes to xylenes; ethyl acetate to vinyl acetate; 2,4,4-trimethylpentane to xylenes; and the like.

The preferred compounds to be dehydrogenated are hydrocarbons with a particularly preferred class being acyclic non-quaternary hydrocarbons having 3 to 5 carbon atoms or ethyl benzene and the preferred products are propane, n-butene-1 or 2, butadiene-1,3, vinyl acetylene, 2-methyl-1-butene, 3-methyl-1-butene, 3-methyl-2-butene, isoprene, styrene or mixtures thereof. Especially preferred as feed are n-butene-1 or 2 and the methyl butenes and mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about atmospheric pressure or sub-atmospheric pressure. Generally the total pressure will be between about 1 p.s.i.a. and about 75 p.s.i.a. Preferably the total pressure will be less than about 50 p.s.i.a.

The temperature of the dehydrogenation reaction will generally be in a range of about 350° to 700° C with excellent results being obtained in the range of 400° to 650° C. The gaseous reactants can be conducted through the reaction chamber at a fairly wide range of flow rates. The optimum flow rates will be dependent upon such variables as the temperature of reaction, pressure, particle size of the catalyst, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually the LHSV will be between 0.15 and about 5. For calculation, the volume of a fixed bed dehydrogenation zone containing the catalyst is that original void volume of reactor space containing catalyst.

The dehydrogenation may be carried out in a series of cycles which comprise dehydrogenation of a suitable feed over the catalysts of the invention under the conditions as defined for a period of time, usually about 6 to 12 minutes followed by a regeneration cycle during which the coke deposited from the dehydrogenation is burnt off. The regeneration can be longer or shorter than the dehydrogenation cycle as needed to remove the coke, usually about 6 to 12 minutes will be sufficient. The coke is removed by passing oxygen at a temperature of 550° to 650° C. over the catalyst. A convenient source of oxygen is air, however, pure oxygen or a mixture of oxygen with inert gases, such as nitrogen, either in the same or different proportions as air, can be used.

The following Examples are submitted to demonstrate the operation of the invention. The process was carried out at atmospheric pressure, i.e., about 15 p.s.i.a. The presence of the chromite structure was established for the catalysts by X-ray analysis as described previously. In the Examples, percents are by weight except that results are given as mol percents. Analysis of the products was by gas-liquid chromatography.

EXAMPLES

Catalyst Preparation

Non-Halogen Catalysts 234.2 gms of hydrous Cr(III) oxide (assay as $Cr_2O_3$ = 64.9 wt %) and 93.8 gms of magnesium carbonate (Marinco CL, Merck Chem, Div., Merck & Co., Inc., Rahway, N.J. Lot N-12, assay as MgO = 43.0 wt %) were slurried together in a 1-qt. Waring blender for 15 minutes using demineralized water as the slurrying medium. The slurry was transferred to a Vycor evaporating dish and dried overnight in an oven at ~ 120° C. The dried cake was crushed to sub 20 mesh particles and divided into three equal portions. One portion was calcined to 800° C. (in a Vycor combustion tube) in an atmosphere of nitrogen (Cat. A). A second portion was calcined to 800° C in an atmosphere of oxygen (Cat. B) and the third portion was calcined to 800° C in air (Cat. C). The calcinations took about 1½ to 2 hours.

Halogen Modified Catalysts

The procedure described above for the non-halogen catalyst was repeated with the exception that a portion of the magnesium carbonate was replaced with an equal-molar amount of magnesium chloride. Thus, 84.4 gms of magnesium carbonate, 234.2 gms of hydrous Cr (III) oxide and 20.4 gms of magnesium chloride (Baker Analyzed Reagent Magnesium Chloride, assay as $MgCl_2 \cdot 6H_2O$ = 99.8%) were slurried in demineralized water and then worked up as described above: calcination to 800° C in $N_2$ (Cat. D) calcination to 800° C in $O_2$ (Cat. E).

Each catalyst (Cat. A–E) was modified by Aluminum and deposited on AMC support as follows:

50 gms of 7-9 mesh AMC support, 40 gms of calcined $MgCr_2O_4$ and 21.0 gms of Baker Analyzed Reagent Aluminum Sulfate (Lot No. 45438, assay as $Al_2(SO_4)_3 \cdot 16H_2O$ = 102.8 wt. %) were slurried in demineralized water and heated to dryness to deposit the actives on the AMC support.

ISOTHERMAL ATMOSPHERIC REACTOR

The reactor for each exemplary run reported below was a 29 × ¾ inch Vycor tube equipped with a heating mantle and appropriate equipment. A 40 cc bed of catalyst was placed in the reactor and reactant feed (or regenerative air) added at the bottom of the reactor with product coming off overhead. The catalyst was heated to the reaction temperature in a nitrogen atmosphere. The process was carried out automatically with a make cycle (dehydrogenation) of 9 minutes and 9 minutes oxygen regeneration and repeat of the cycle. This gave a total cyclic time of 18 minutes. When desired, the partial pressure of the hydrocarbon feed during the reaction cycle was reduced below atmospheric by dilution with nitrogen. The total effluent from either or both cycles was collected in an inflatable collecting device and analyzed by gas chromatography. Alternately, the effluent from the regeneration cycle was passed through a calibrated infrared analyzer to determine the amount of $CO_2$ produced during regeneration (coke burn-off). By either method of analysis the amount of coke deposited on a catalyst during the reaction cycle was determined and could be taken into account when calculating the overall activity and selectivity of a catalyst. The temperatures were controlled by a thermoelectric temperature controller and recorded on a Leeds and Northrup 24-point recorder.

In the following runs the feed was 99 mol %+n-butane, LHSV = 1.0, T max = ~ 600° C, partial pressure of the n-butane feed (n - butane + $N_2$) = 0.33 atom. The results are given in the table below as C (conversion), S (selectivity), Y(yield), Bu (butadiene), Y = C X S. Samples were on stream for 26 hours.

chromium is present with said precursors during the formation of said chromite.

8. The process according to claim 7 wherein the halogen is chlorine, bromine or iodine.

9. The process according to claim 8 wherein 0.0001 to 1.0 mol of halogen per atom of chromium is present.

10. The process according to claim 8 where the halogen is chlorine.

11. The process according to claim 8 wherein the atmosphere is essentially nitrogen.

12. The process according to claim 11 wherein the halogen is chlorine.

| EXAMPLE | CATALYST COMPOSITION | C | RESULTS, mol% | | | |
|---|---|---|---|---|---|---|
| | | | S | | Y | |
| | | | Bu | Bd | Bu | Bd |
| 1 | Cat. C - No halogen calcined in air | 34.4 | 72.9 | 21.3 | 25.1 | 7.3 |
| 2 | Cat. B - No halogen calcined in oxygen (100%) | 47.4 | 69.9 | 15.6 | 33.2 | 7.4 |
| 3 | Cat. A - no halogen calcined in nitrogen | 53.9 | 67.6 | 15.4 | 36.5 | 8.3 |
| 4 | Cat. E - halogen calcined in oxygen (100%) | 52.3 | 72.1 | 16.8 | 37.7 | 8.8 |
| 5 | Cat. D - halogen calcined in nitrogen | 68.1 | 67.1 | 14.8 | 45.7 | 10.1 |

The invention claimed is:

1. In a process for the preparation of magnesium chromite for use in cyclic dehydrogenation comprising the steps of intimately mixing precursors of magnesium chromite and heating said precursors to a temperature in the range of 550° to 900° C said precursors being nitrates, hydroxides, hydrates, oxalates, carbonates, acetates, formates, halides or oxides, wherein the improvement comprises forming said chromite in an essentially inert atmosphere of nitrogen, helium, neon, argon, krypton, xenon, radon or mixtures thereof, which may contain up to about 3 mole percent of a reactive gas as determined in a static atmosphere.

2. The process according to claim 1 wherein said precursors are intimately mixed in a slurry.

3. The process according to claim 1 wherein the atmosphere is essentially nitrogen.

4. The process according to claim 1 said magnesium chromite has the general formula Me $Cr_2 O_4$, wherein Me comprises at least 50 atomic percent Mg and one or more of the divalent ions of Ca, Sr, Ba, Fe, Mn, Co, Ni, Cu, Zn or Cd.

5. The process according to claim 1 wherein the temperature is in the range of 600° to 800° C.

6. The process according to claim 3 wherein said precursors are finely divided intimately mixed in a slurry.

7. The process according to claim 1 wherein a catalytic amount of 0.0001 to 1.0 mol of halogen per atom of 13. The process according to claim 7 wherein said halogen is initially present in a solid compound in intimate mixture with said precursor.

14. In a process of preparing magnesium chromite for use as dehydrogenation catalyst comprising the steps of:
slurring in water, finely divided water insoluble precursors of magnesium chromite to form an intimate mixture thereof said precursors being nitrates, hydroxides, hydrates, oxalates, carbonates, acetates, formates, halides or oxides, drying said precursors, heating said intimate mixture of precursors to a temperature in the range of 550° to 900° C to form magnesium chromite, and intimate admixing therewith a promoting amount of aluminum wherein the improvement comprises forming said chromite in an essentially inert atmosphere of nitrogen, helium neon, argon, krypton, xenon, radon or mixtures thereof which may contain up to about 3 mol percent of a reactive gas as determined in a static atmosphere.

15. The process according to claim 51 wherein 0.0001 to 1.0 mol of a halogen per atom of chromium selected from the group consisting of chlorine, bromine and iodine is present during said heating in intimate contact with said precursors.

16. The process according to claim 15 where said atmosphere comprises essentially nitrogen.

17. The process according to claim 16 where said halogen is chlorine.

* * * * *